US008267864B2

(12) United States Patent
Kishimoto

(10) Patent No.: US 8,267,864 B2
(45) Date of Patent: Sep. 18, 2012

(54) ULTRASONIC DIAGNOSTIC APPARATUS

(75) Inventor: Shinji Kishimoto, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 1170 days.

(21) Appl. No.: 10/552,471

(22) PCT Filed: Apr. 2, 2004

(86) PCT No.: PCT/JP2004/004885
§ 371 (c)(1),
(2), (4) Date: Oct. 7, 2005

(87) PCT Pub. No.: WO2004/089221
PCT Pub. Date: Oct. 21, 2004

(65) Prior Publication Data
US 2007/0112266 A1    May 17, 2007

(30) Foreign Application Priority Data

Apr. 8, 2003  (JP) .................................. 2003-104329
Aug. 8, 2003  (JP) .................................. 2003-290491

(51) Int. Cl.
*A61B 8/00* (2006.01)
(52) U.S. Cl. ........ 600/437; 600/440; 600/441; 600/443; 600/449; 128/915; 128/916
(58) Field of Classification Search ................. 600/437, 600/441, 443, 449, 440; 128/200.16, 916
See application file for complete search history.

(56) References Cited

U.S. PATENT DOCUMENTS

| | | | |
|---|---|---|---|
| 4,603,702 A * | 8/1986 | Hwang et al. | 600/437 |
| 4,694,680 A * | 9/1987 | Takeuchi et al. | 73/1.82 |
| 4,708,127 A * | 11/1987 | Abdelghani | 601/2 |
| 4,945,767 A * | 8/1990 | Shirasaka | 73/610 |
| 5,230,339 A * | 7/1993 | Charlebois | 600/437 |
| 5,517,994 A * | 5/1996 | Burke et al. | 600/437 |
| 5,538,004 A * | 7/1996 | Bamber | 600/443 |
| 5,654,509 A | 8/1997 | Miele et al. | |
| 5,718,228 A * | 2/1998 | Hiruta et al. | 600/437 |
| 6,592,521 B1 * | 7/2003 | Urbano et al. | 600/441 |

(Continued)

FOREIGN PATENT DOCUMENTS

JP   60-177766   9/1985

(Continued)

*Primary Examiner* — Tse Chen
*Assistant Examiner* — Vani Gupta
(74) *Attorney, Agent, or Firm* — Antonelli, Terry, Stout & Kraus, LLP.

(57) ABSTRACT

An ultrasonograph comprising a probe (10) for transmitting/receiving an ultrasonic wave to/from a subject, a transmitting section (12) for supplying a drive signal to the probe (10), a receiving section (12) for receiving a reflection echo signal outputted from the probe (10), image constructing sections (17, 19, 21) for reconstructing a diagnosis image from the received reflection echo signal, a displaying section (25) for displaying the reconstructed diagnosis image, and a control section for controlling the other sections, wherein the rise of temperature of the probe (10) is suppressed by adequately judging whether the probe (10) is left in the air or not. The ultrasonograph further comprises a judging section (22) for judging from diagnosis image information whether or not the probe (10) is left in the air. If the judging section (22) judges that the probe (10) is left in the air, the control section (26) controls the drive signal supplied from the transmitting section to the probe (10) so as to suppress the rise of temperature of the probe (10).

10 Claims, 12 Drawing Sheets

U.S. PATENT DOCUMENTS

| | | | |
|---|---|---|---|
| 6,602,196 B2 * | 8/2003 | Suzuki et al. | 600/455 |
| 7,225,965 B2 * | 6/2007 | Johansen | 228/1.1 |
| 2002/0082501 A1 | 6/2002 | Emery | |

FOREIGN PATENT DOCUMENTS

| | | | | |
|---|---|---|---|---|
| JP | 02154745 A | * | 6/1990 | |
| JP | 05-000138 | | 1/1993 | |
| JP | 05000138 A | * | 1/1993 | |
| JP | 05-253225 | | 10/1993 | |
| JP | 05253225 A | * | 10/1993 | |
| JP | 10-052428 | | 2/1998 | |
| JP | 10-108864 A | | 4/1998 | |

* cited by examiner

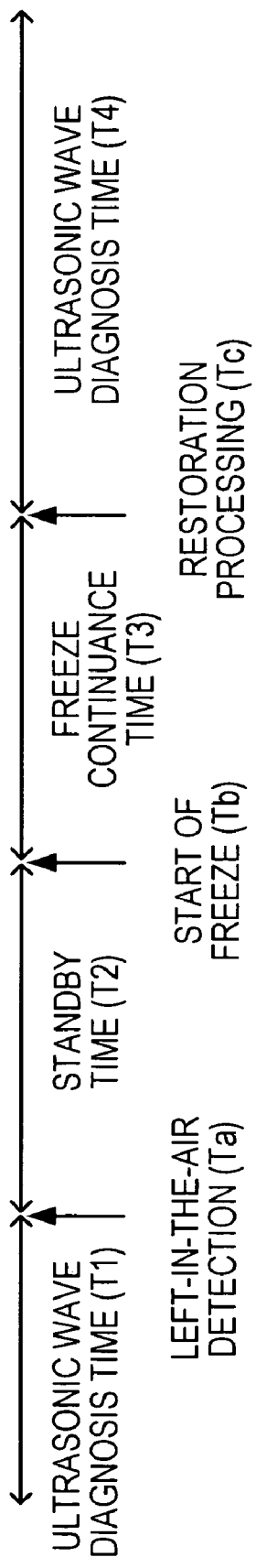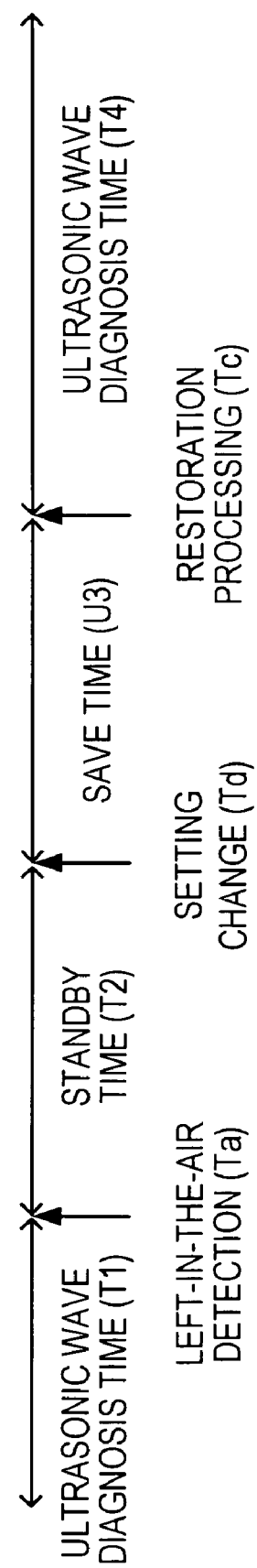

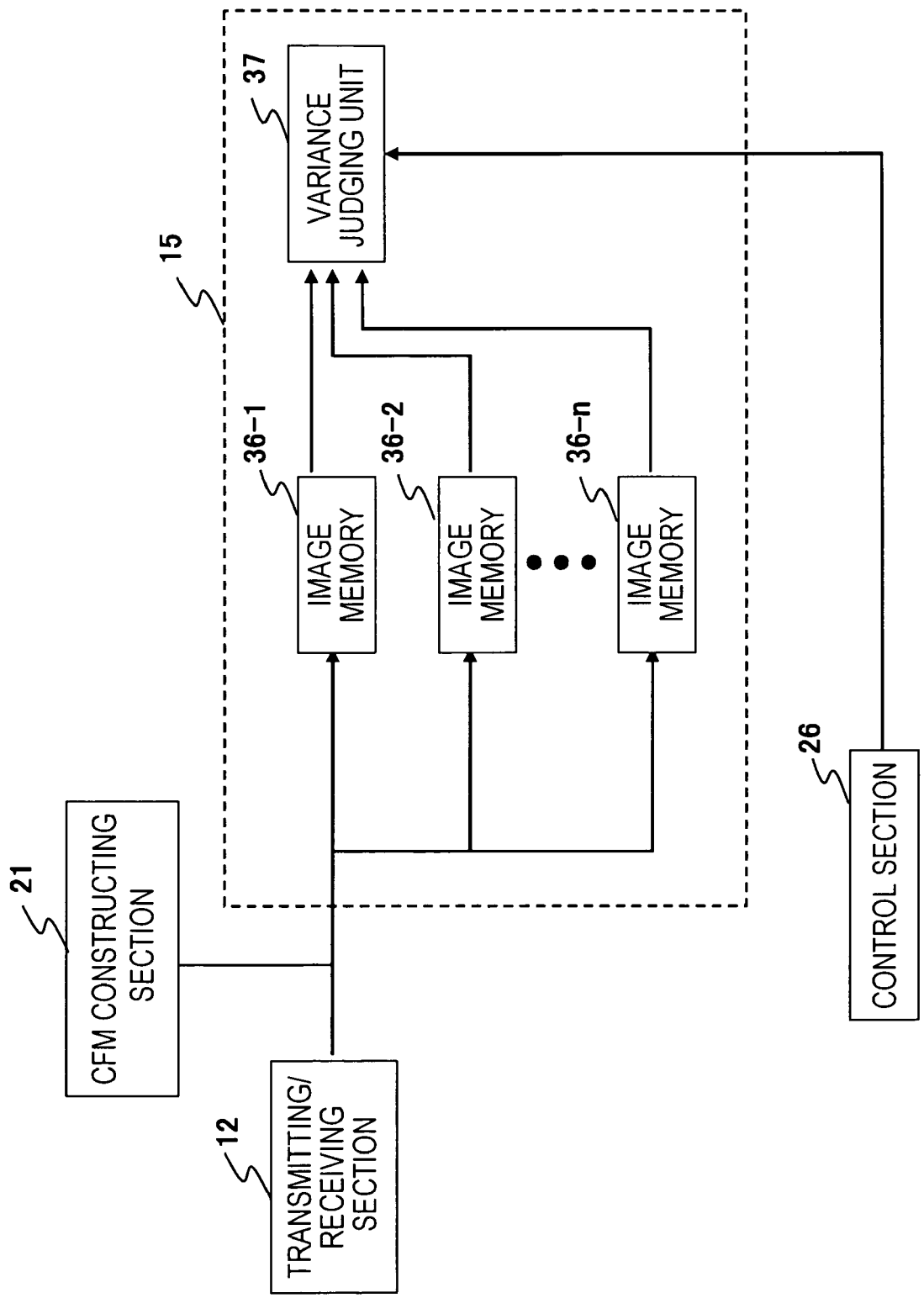

DISPLAY WARNING IN JAPANESE OR FOREIGN LANGUAGE.
AUTOMATICALLY REDUCE THE NUMERICAL VALUE OF "X".

FIG. 12
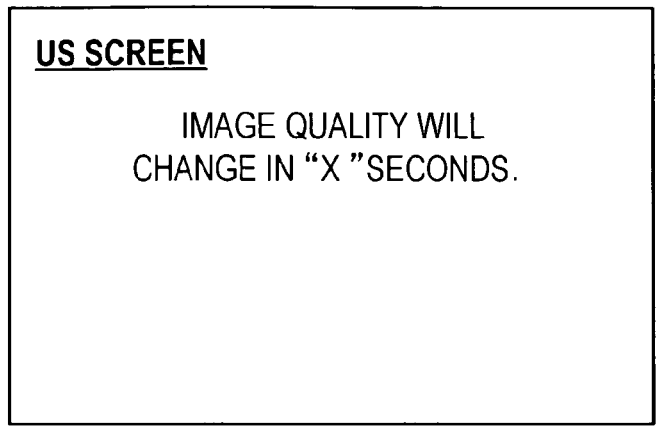
CAUSE CHARACTERS TO BLINK, INCREASE SIZE,
OR TO DISPLAY NEW SYMBOL WHEN
REMAINING TIME HAS BECOME SHORT.
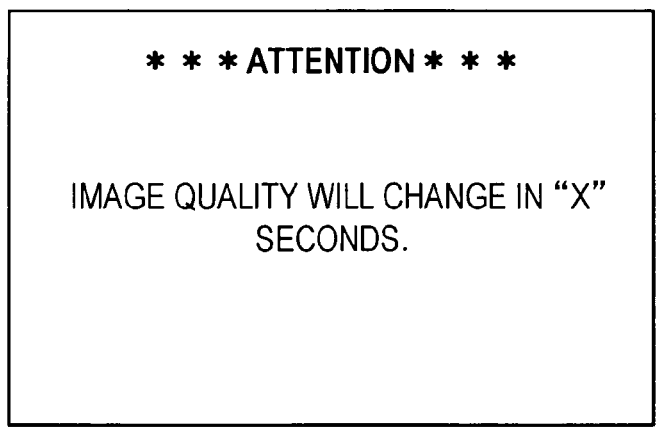
FIG. 16
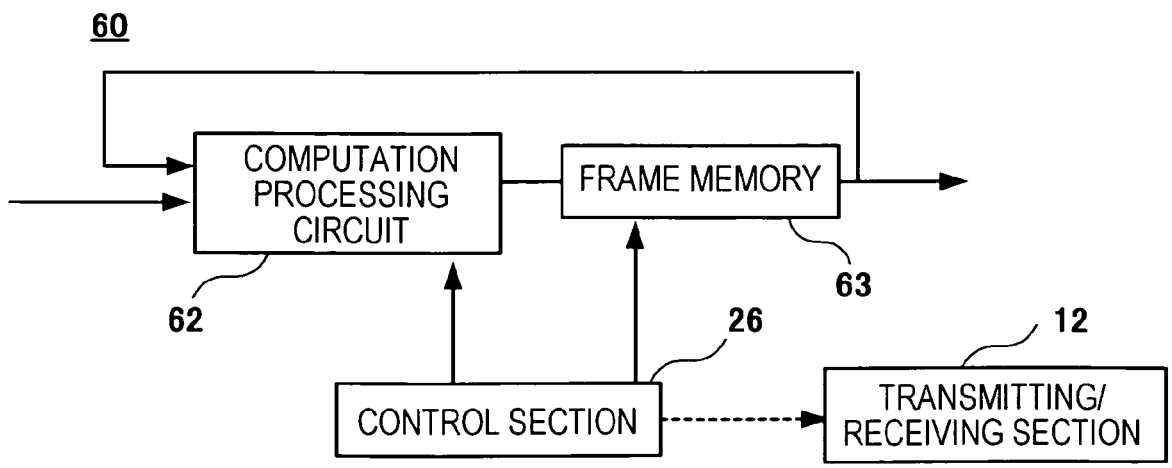

ULTRASONIC DIAGNOSTIC APPARATUS

TECHNICAL FIELD

The present invention relates to an ultrasonic diagnostic apparatus, and in particular to technology that prevents the deterioration of a probe.

BACKGROUND ART

An ultrasonic diagnostic apparatus is an apparatus that brings a probe into contact with the body surface of a test subject, repeatedly irradiates an observation sight with ultrasonic waves via the probe, receives a reflection echo signal generated from the test subject, and reconstructs an ultrasound image (e.g., a tomogram).

In such ultrasonic diagnostic apparatus, when the ultrasonic waves are continuously transmitted while the probe is separated from the body surface of the test subject (called "left in the air" below), the energy of the transmitted ultrasonic waves changes to thermal energy and the temperature in the vicinity of the surface of the probe (e.g., the ultrasonic wave transmittance window, etc.) rises. As a result, sometimes deterioration arises, such as a member like rubber that forms the probe separating, because a thermal heat cycle arises in the probe.

In order to prevent such a temperature rise, conventionally the transmission of the ultrasonic waves has been automatically stopped when the operation console has not been operated for a certain period of time or greater. For example, a timer is activated when an operation has not been conducted, it is assumed that the probe is left in the air when the timer counts a preset period of time, and the temperature of the probe is prevented from rising by stopping the transmission of the ultrasonic waves (hereinafter referred to as freezing) (Patent Document 1: Japanese Patent Application Publication No. 64-68239).

Also, when a change in the temperature of the surface of the probe is recorded and the temperature rise is calculated and the temperature rise exceeds a stipulated value, the transmission output is set to be within the stipulated value (Patent Document 2: Japanese Patent Application Publication No. 2000-5165).

However, according to the ultrasonic diagnostic apparatus described in Patent Document 1, when the operation console has not been operated for the certain period of time, it is assumed that the probe is left in the air, so that sometimes the judgment that the probe is left in the air is not accurate. For example, when the probe is brought into contact with the test subject and diagnosis is conducted over a relatively long period of time, it is assumed that the probe is left in the air and that freezing has started because there is no command from the operation console, which is a drawback.

Also, according to the ultrasonic diagnostic apparatus described in Patent Document 2, there is no sense of real time and the transmission output cannot be set before the temperature of the probe rises. Thus, the ultrasonic diagnostic apparatus is lacking in safety.

The problem of the present invention is to accurately judge that the probe is left in the air and suppress a rise in the temperature of the probe.

DISCLOSURE OF THE INVENTION

In order solve this problem, the invention of the present application provides an ultrasonic diagnostic apparatus comprising: a probe that transmits/receives ultrasonic waves to/from a test subject; a transmitting section that supplies a drive signal to the probe; a receiving section that receives a reflection echo signal outputted from the probe; an image constructing section that reconstructs a diagnostic image on the basis of the received reflection echo signal; a display section that displays the diagnostic image constructed by the image constructing section; and a control section that controls these sections, wherein the ultrasonic diagnostic apparatus includes a judging section that judges, on the basis of the diagnostic image information, that the probe is left in the air, and when the judging unit judges that the probe is left in the air, the control section controls the drive signal supplied to the probe from the transmitting section so as to suppress a rise in the temperature of the probe.

BRIEF DESCRIPTION OF THE DRAWINGS

FIG. 7 are times chart relating to processing.

FIG. 10 is a diagram showing the configuration of a CFM judging section.

FIG. 12 is a diagram showing examples of displays on a screen.

FIG. 16 is a diagram showing the configuration of a frame correlation processing circuit.

BEST MODES FOR IMPLEMENTING THE INVENTION

Embodiments of the invention will be described below using the drawings.

Embodiment 1

First, a first embodiment that judges that a probe is left in the air will be described with reference to FIGS. 1 to 7.

Figure 1:
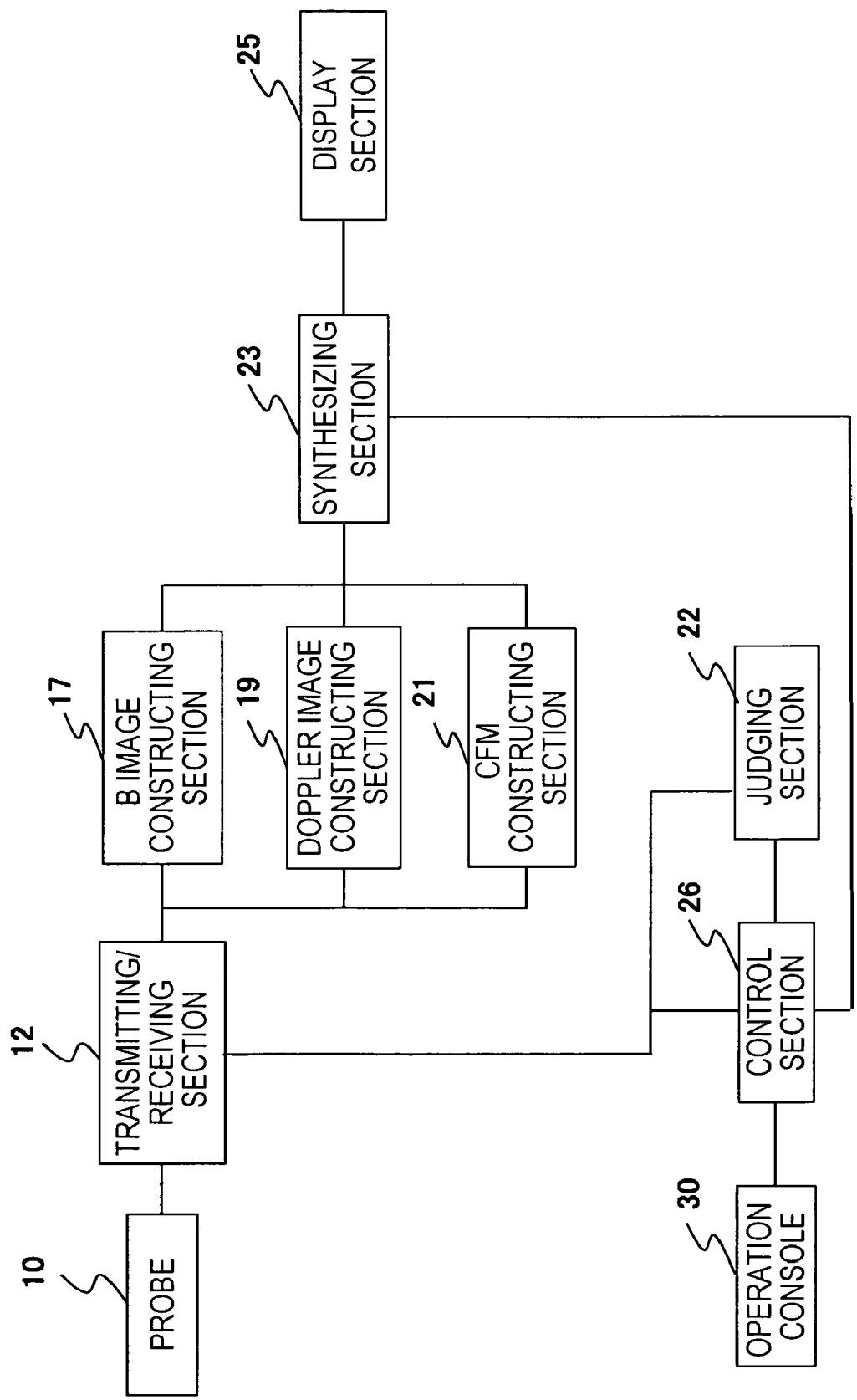
FIG. 1 is a diagram showing a block diagram of an ultrasonic diagnostic apparatus to which the present invention has been applied.

As shown in FIG. 1, an ultrasonic diagnostic apparatus 1 of the present embodiment is configured to include: a probe 10, a transmitting/receiving section 12 including a transmitting unit, a receiving circuit, an AD conversion unit, and a phasing adding unit; a B image constructing section 17, a Doppler image constructing section 19, and a CFM constructing section 21, each of which includes an image constructing unit, a frame memory that is an image recording unit, and a DSC (digital scan converter); a synthesizing section 23 that synthesizes these images; a judging section 22 that judges that the probe is left in the air; a display section 25 including a monitor; a control section 26 that controls these constituent elements; and an operation console 30. The control section 26 includes a change control function for outputting a command to the transmitting/receiving section 12 on the basis of a signal from the judging section 22 and a display control function for outputting a display command to the display section 25. The schematic diagram of the control section 26 and the other sections shows only the minimum elements necessary for description.

The operation of the ultrasonic diagnostic apparatus 1 configured in this manner will be described. First, the probe 10 is brought into contact with the body surface of a test subject. Next, a drive signal for ultrasonic wave transmission is supplied to the probe 10 from the transmitting/receiving section 12 on the basis of a command from the control section 26.

The supplied drive signal is converted into an ultrasonic wave by the probe 10, and the probe 10 irradiates a region of the test subject including an observation site with the converted ultrasonic wave. The ultrasonic wave generated from the irradiated region is received by the probe 10 and converted into a reflection echo signal. The converted reflection echo signal is received by the transmitting/receiving section 12 and then converted into a digital signal by the AD conversion unit. The phase of the converted digital signal is phased by the phasing adding unit, and the digital signal is reconstructed by the B image constructing section 17 into a tomogram (called a "B image" below), which is a diagnostic image. A Doppler signal included in the digital signal is reconstructed by the Doppler image constructing section 19 into a Doppler image, and a CFM image is reconstructed by the CFM constructing section 21.

The reconstructed B image is sequentially stored in the frame memory. Image information of the B image stored in the frame memory is detected by the judging section 22, converted by the DSC into a display-use signal, and displayed on the monitor of the display section 25. The Doppler signal and the CFM are similarly displayed on the monitor of the display section 25.

Figure 2:
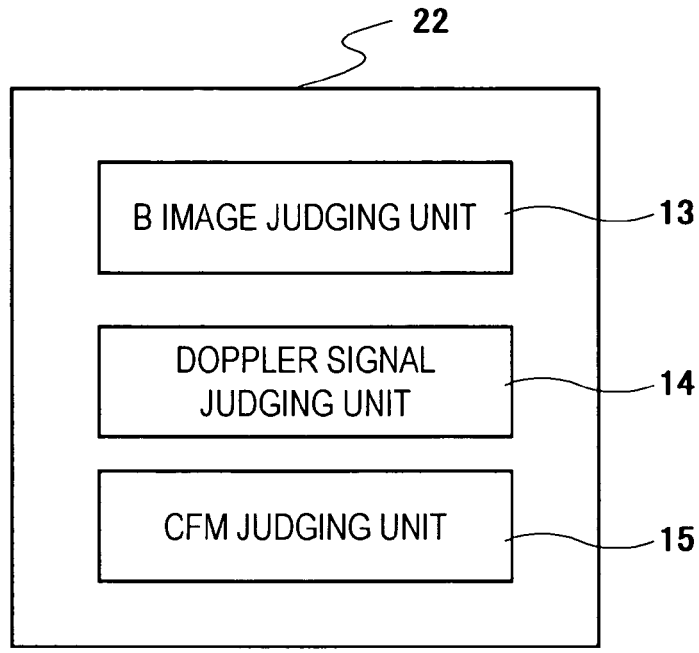
FIG. 2 is a diagram showing the configuration of a judging section.

Next, the configuration and operation of the judging section 22 will be described using FIGS. 2 to 5. As shown in FIG. 2, the judging section 22 is configured by a B image judging unit 13, a Doppler signal judging unit 14, and a CFM judging unit 15, and judges with the plural judging units so as to be suited to the respective image information.

Figure 3:
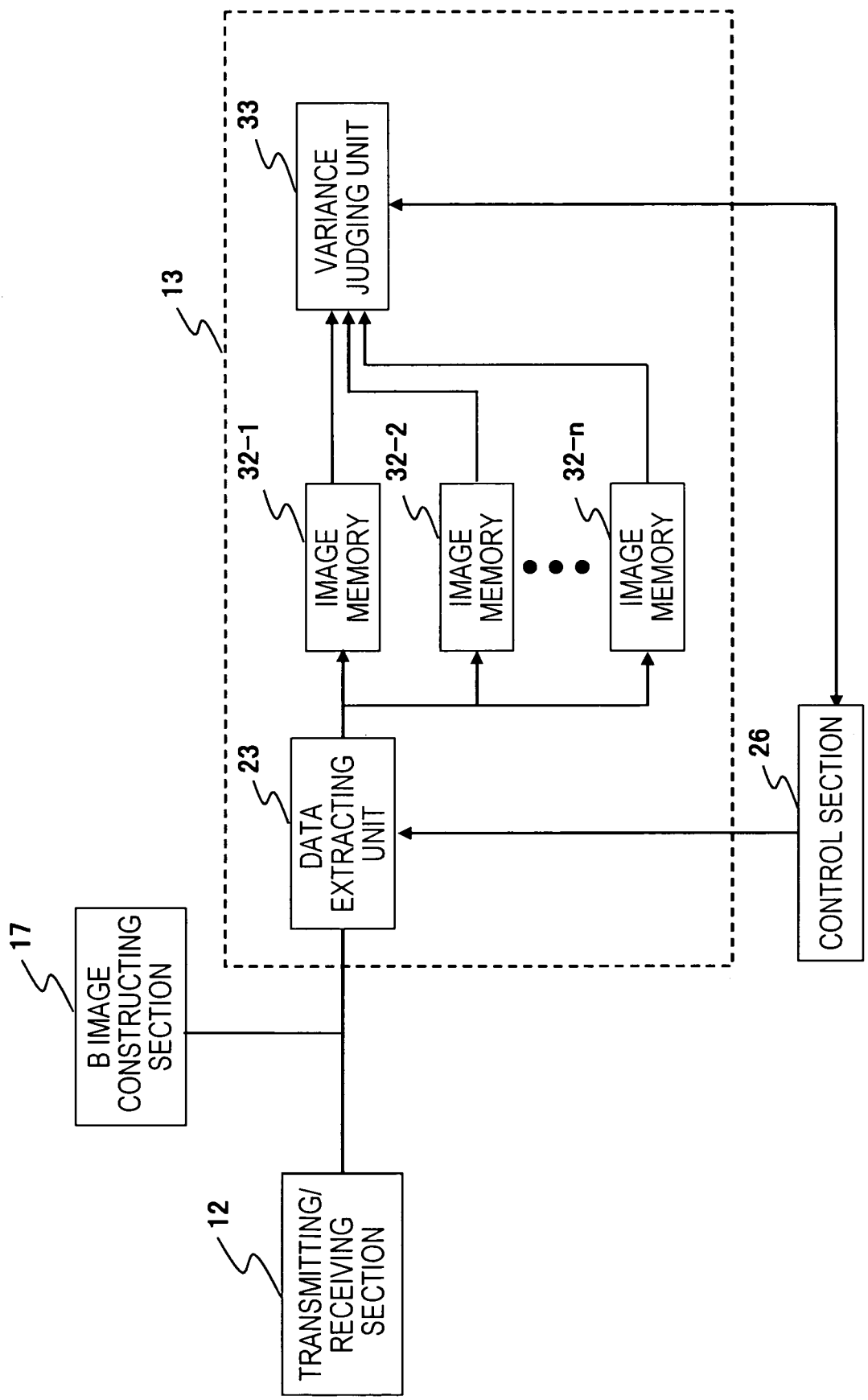
FIG. 3 is a diagram showing the configuration of a B image judging section.
Figure 5:
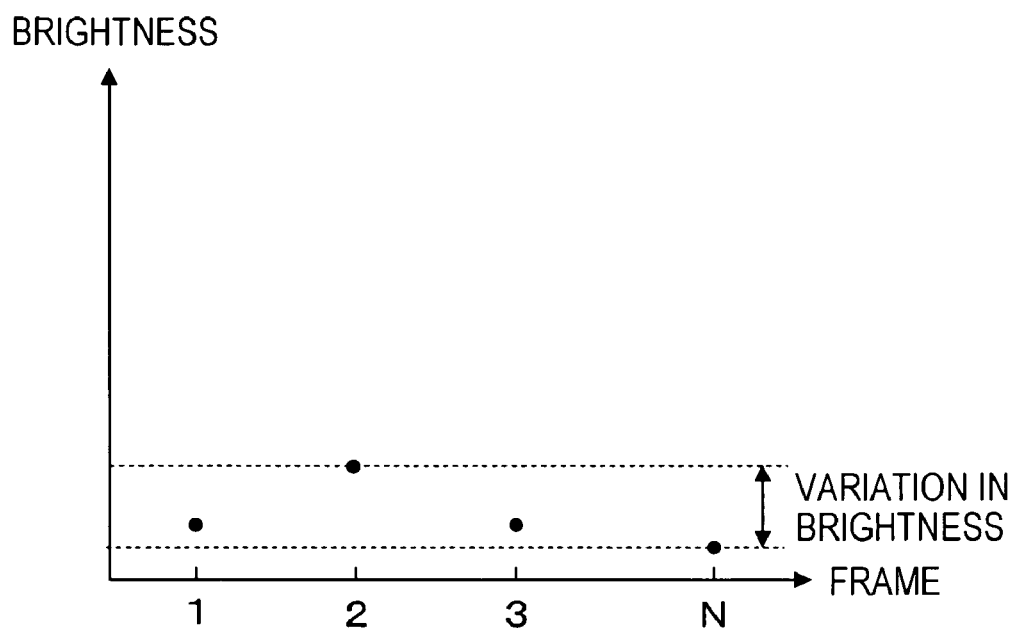
FIG. 5 is a diagram for describing a judging method.

As shown in FIG. 3, the B image judging unit 13 is configured to include a data extracting portion 23, image memories 32-1 to 32-n, and a variance judging portion 33 including a brightness calculating circuit, a variance circuit and a variance calculating circuit. Here, "n" represents an optional natural number.

Figure 4:
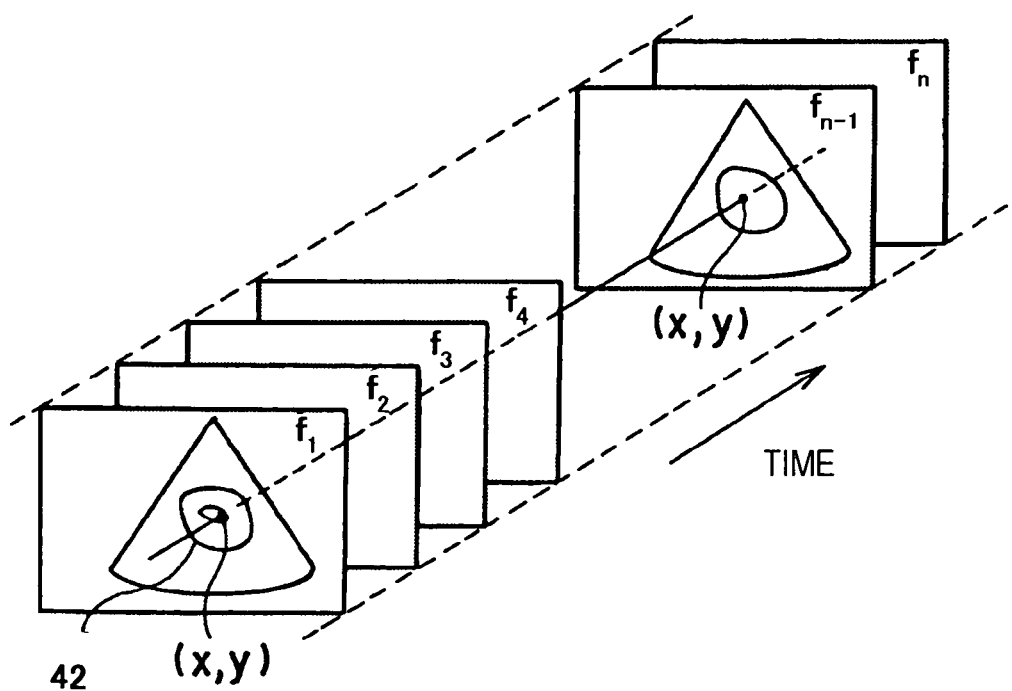
FIG. 4 is a conceptual diagram for describing a judging method.

As shown in FIG. 4, temporally continuous plural B images $f_1$ to $f_n$ are read from the frame memory, and the read B images $f_1$ to $f_n$ are arranged in order and stored in the image memories 32-1 to 32-n. The B images stored in the image memories 32 are simultaneously read on the basis of a command from the control section 26. The entire image of each of the read B images, or the brightness of each pixel in a preset area of interest 42, is integrated by the brightness calculating circuit. The integrated brightness, i.e., the integrated value, is inputted to the variance calculating circuit via the variance circuit together with the B images from the image memories 32-1 to 32-n. The variance calculating circuit determines the variance of the data of the same number (x, y) in regard to the image data of the plural frames $f_1$, $f_2$, etc., to $f_n$. The integrated value referred to here is a value where the temporal brightness level in the entire image or the region of interest has been integrated and indexed, which means that when the integrated value is high, the image is whitish. Also, the variance is a value where inter-frame variance in the brightness has been indexed, which means that when the variance is large, the variation in the brightness is relatively large.

Next, the calculation of the variance will be described. Coordinates are set in the data extracting portion 23 via the control section 26 from the operation console 30. The data extracting portion 23 reads a reflection brightness signal obtained from the ultrasonic wave transmitting/receiving section and extracts the image information of the set specific coordinates. The data extracting portion continuously records, in the memories 1, 2, etc., to memory n, the brightness information of the specific coordinates of the temporally continuous frames and continues updating per frame. The image information is synchronized with the frame display timing or single frame transmission timing and simultaneously outputted. In the brightness graph shown in FIG. 5, the variance computing circuit compares the brightness in n frames and calculates the variance from the brightness information at the same coordinates in the n frames simultaneously outputted. The variance computing circuit outputs the variance to the variance judging portion 33 at the same time as it calculates the variance. The variance judging portion 33 compares the size of the computed variance and with that of a preset variance (threshold). For the variance (threshold), a variance (threshold) actually measured beforehand by actual measurement may be determined and recorded in a storage section. Specifically, the variance is measured as having characteristics, such as "brightness is high and variance is large" when the probe is left in the air as compared to when the test subject is imaged, and the variance is stored in the storage section. The B image judging unit 13 outputs a left-in-the-air detection signal when the integrated value is a high level for a certain period of time or greater in the entire image or the region of interest, or when the calculated variance is larger than the set variance (threshold). The setting of the conditions of the integrated value and the variance of the B image judging unit 13 can be optionally conducted by the operator with the operation console 30.

However, the drive signal that is generated such that the temperature of the probe 10 does not rise is dependent on the type of the probe 10. Thus, the ultrasonic diagnostic apparatus 1 may be configured to understand the type of connected probe, send various information to the control section 26, and calculate the variance, and the control section 26 may correlate and record the various information with the probe and store it in the storage section as the threshold when the probe is left in the air or as a reference value. The variance may also be calculated by n-number of data by a common statistical method, or estimated from a graph pattern. Also, because the fluctuation in the image is relatively large in a B image in an observation region whose depth is deep (or shallow), the B image judging unit 13 may be configured so that when the brightness of the B image is detected, the B image judging unit 13 integrates the brightness limited to the region of interest 42 excluding that region and outputs the left-in-the-air signal by that integrated value. Thus, the precision of detecting the brightness can be improved, the amount of data to be computed can be reduced, and the speed of detection processing can be improved. In this case, the brightness of the pixels may also be integrated across the entire B image.

In this manner, in the first embodiment, the ultrasonic wave transmitted from the probe 10 is multiply reflected in the vicinity of the ultrasonic wave transmittance window when the probe is left in the air, whereby the B image constructed by the image constructing section becomes whitish with a relatively high brightness level, and the judgment of whether the probe is left in the air is conducted using this image information.

Next, the processing sequence that suppresses a rise in the temperature of the probe 10 will be described with reference to FIGS. 6, 7(A) and 11.

Step 101: In regard to the probe 10 being left in the air, when the judging section 22 detects (Ta) that the integrated value of the brightness of the B image has exceeded the preset threshold for a certain period of time or greater, or when the data calculated variance is greater than the set variance (threshold) it is assumed that the probe 10 is left in the air. On the other hand, when the integrated value of the brightness does not exceed the preset threshold, or when the computed variance is smaller than the set variance (threshold), the processing of step 101 is repeatedly conducted. This threshold is set beforehand with the operation console 30 so that the brightness of the B image becomes whitish when this value has been exceeded.

At the same time that the judging section 22 detects the brightness of the B image, the drive condition of the probe 10 (e.g., the transmission voltage relating to the transmitted ultrasonic wave, the number of transmitted waves, the repetition frequency, the transmission range of the ultrasonic beam, etc.) or the frame rate of the B image, is identified and saved as data in the storage section (not shown).

Step 102: Setting of the Freeze Start Time

The drive condition saved in the processing of step 101 is matched with a drive condition (mode where the transmission voltage is high, mode where the number of transmitted waves is high, mode where the repetition frequency is large, mode where the scanning range of the ultrasonic beam is narrow, etc.) where a rise in the temperature of the probe 10 occurs that was actually measured beforehand in the design stage, or with the frame rate of the B image. On the basis of this matching result, the starting time (Tb) of the freezing of the ultrasonic wave transmission system is set.

Step 103: Display of Warning

Figure 11:
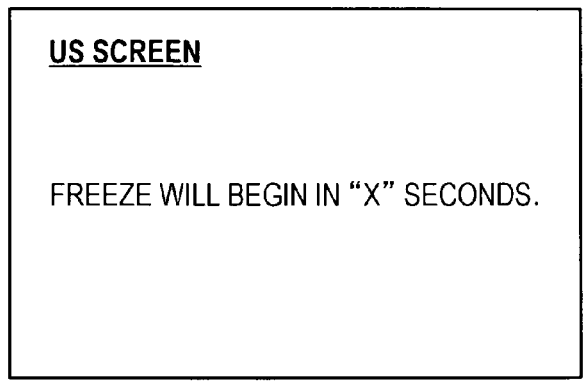
FIG. 11 is a diagram showing an example of a display on a screen.

As shown in FIG. 11, the control section 26 outputs a command to the display section 25, and on the basis of that command, the period of time until freezing is started (standby time: T2) is displayed on the monitor with a character string in the Japanese language or a foreign language.

Step 104: Detection of Command from Operation Console 30

While the standby time (T2) is being counted by the timer, it is detected whether or not the operation console 30 (e.g., keys, trackball, dial, pointing device, etc.) has been operated. If the operation console 30 has been operated, the timer that had been counting is initialized and the processing of step 102 is again conducted. If the operation console 30 has not been operated, on the other hand, the processing of step 105 is conducted. If a preset specific operation has been conducted (e.g., a specific key has been pushed), the processing returns to step 101.

Step 105: Counting of Standby Time (T2)

When it is detected that the standby time (T2) has reached zero, the freeze processing of step 106 is conducted. When this is not detected, the processing of step 105 is again conducted.

Step 106: Start of Freeze

The control section 26 outputs a command to the transmitting/receiving section 12 and the drive signal supplied to the probe 10 from the transmitting/receiving section 12 is updated, whereby freezing of the ultrasonic wave transmission system is started and the transmission of the ultrasonic wave from the probe 10 is stopped (Tb).

Step 107: Resumption of Ultrasound Diagnosis

While the freeze is being continued, it is detected whether or not there is an operation from the operation console 30. When there is an operation (Tc), the drive signal supplied to the probe 10 from the transmitting/receiving section 12 is returned to the original drive signal, whereby the freezing of the ultrasonic wave transmission system is released and the ultrasonic wave for diagnosis is continuously transmitted from the probe 10 (T4). Thus, the diagnostic efficiency can be improved because ultrasound diagnosis can be resume data desired time on the basis of the intent of the examiner.

The processing of steps 101 to 107 is conducted by the control section 26, whereby it can be accurately judged that the probe 10 is left in the air. When it is detected that the probe 10 is left in the air, a rise in the temperature of the probe 10 can be suppressed by stopping the drive signal supplied to the probe 10 from the transmitting/receiving section 12 and starting the freezing of the ultrasonic wave transmission system so that the transmission of the ultrasonic wave stops.

Also, the fact that freezing will start can be visually understood because the period of time until freezing is started, i.e., the period of time until the transmission of the ultrasonic wave from the probe 10 is stopped, is displayed on the display section 25. Thus, situations can be prevented where freezing is prevented from occurring counter to the intent of the examiner, or where the ultrasonic wave freeze processing is recognized as a malfunction in the ultrasonic wave transmission system, e.g., the transmitting/receiving section 12. In the present embodiment, as shown in FIG. 7(A), freezing is started after the standby time (T2) has elapsed; however, instead of this, the freezing of the ultrasonic wave transmission system may also be immediately started when it is detected that the probe 10 is left in the air.

Embodiment 2

A second embodiment of the ultrasonic diagnostic apparatus to which the invention is applied will be described using FIGS. 8 to 10. The present embodiment is different from the first embodiment in that, instead of judging that the probe 10 is left in the air from the brightness information of the B image, it is detected that the probe 10 is left in the air on the basis of the Doppler image or the CFM image. The same reference numerals will be given to elements having the same function and configuration as those in the first embodiment, and description thereof will be omitted.

Figure 8:
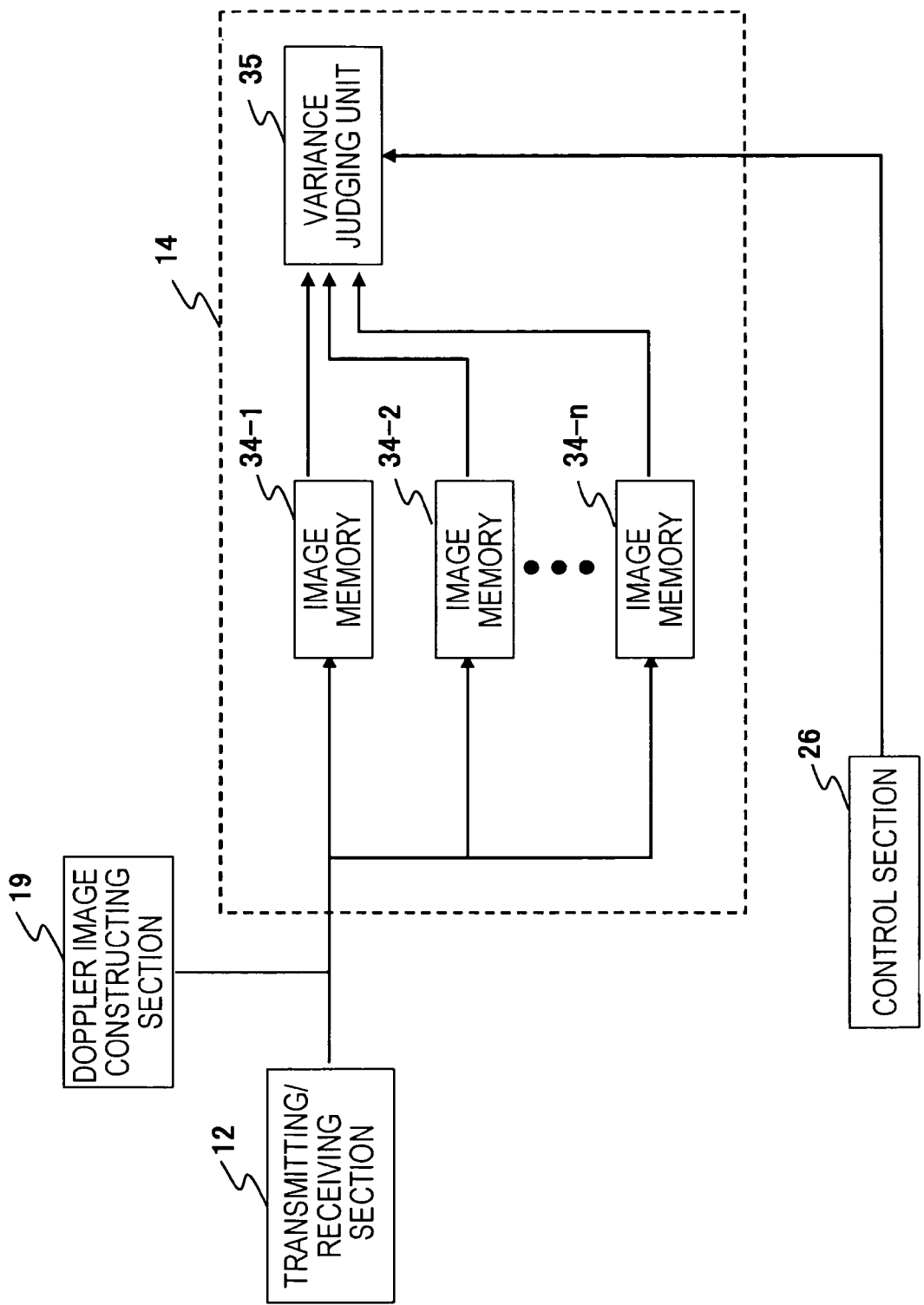
FIG. 8 is a diagram showing the configuration of a Doppler signal judging section.

As shown in FIG. 8, the Doppler signal judging unit 14 of the ultrasonic diagnostic apparatus 1 is configured to be able to judge using a Doppler signal. The Doppler signal judging unit 14 is configured to include image memories 34-1 to 34-n, a Doppler variance circuit and an adding circuit (not shown) and a variance judging portion 35. RF data outputted from the phasing adding unit are reconstructed by the Doppler image constructing section 19 into a Doppler image pertaining to the spectral waveform of blood flow, for example, and the reconstructed Doppler image is stored in the frame memory. The stored Doppler image is read and sequentially arranged and stored in the image memories 34-1 to 34-n. The Doppler images stored in the image memories 34 are simultaneously read on the basis of a command from the control section 26. The variances (variations in image quality) of the simultaneously read Doppler images are calculated by the Doppler variance circuit, and the calculated variances are added by the adding circuit. Then, when the Doppler signal judging unit 14 detects that the added variance exceeds a preset threshold for a certain period of time or greater, it judges that the probe 10 is left in the air and outputs the left-in-the-air detection signal.

Specifically, with respect to a Doppler image acquired when the probe 10 is left in the air, when the Doppler signal judging unit 14 detects an image where there is no spectral waveform in which only noise has appeared, i.e., an image where there is no Doppler signal, the Doppler signal judging unit 14 sets the threshold to switch to when the probe is left in the air, and handles this. Then, when the Doppler signal judging unit 14 judges that the probe 10 is left in the air, it freezes the ultrasonic wave transmission system to prevent the temperature of the probe 10 from rising.

Here, the Doppler signal judging unit 14 can also judge in B mode imaging. The Doppler signal is received for a certain period of time while the B image is imaged, and the Doppler signal judging unit 14 judges with the Doppler signal of that certain period of time. The Doppler signal judging unit 14 detects whether or not the variances of the Doppler signal added in the certain period of time have exceeded the preset threshold, whereby it judges whether or not the probe 10 is left in the air. The control section 26 may also set the Doppler signal judging unit 14 to repeatedly conduct this judging mode.

Instead of the B image judging unit 13 and the Doppler signal judging unit 14, the CFM judging section 15 may judge with the CFM image. The CFM image is displayed using, as video information, the three types of information of the speed, direction, and the variance in the speed of a moving portion inside a living organism. The speed of the moving portion is displayed by brightness, and the direction of the movement of the moving portion is displayed by allocating colors in accordance with the direction. When the probe 10 is left in the air, the phase of the Doppler signal becomes inconsistent at each point in the entire image or the region of interest, so the brightness and color hue are inconsistently displayed. Using this characteristic, the CFM judging section 15 judges that the probe 10 is left in the air on the basis of the variance in the brightness and color hue of the CFM image in the entire image or the region of interest, and outputs the left-in-the-air detection signal. The method of determining the variance is as was described in the preceding embodiment.

Figure 9:
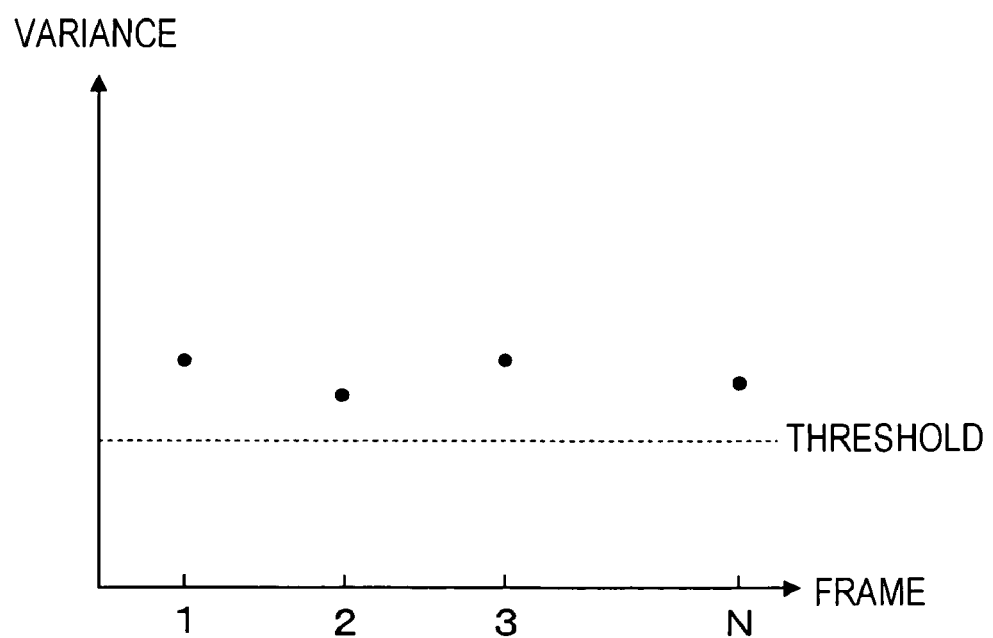
FIG. 9 is a diagram for describing a judging method.

Specifically, the variance in the brightness and color hue is determined using the pixels on the CFM images, and as shown in FIG. 9, it is compared with the preset variance (threshold). Then, the CFM judging section 27 judges whether or not the probe is left in the air on the basis of the comparison result.

Ordinarily in the diagnostic mode, it is difficult to detect that the probe is left in the air because the level of the Doppler signal is low, but this state is easy to detect when the gain of the Doppler signal is raised. Thus, the gain rise time may be optionally set with the operation console 30 in the CFM judging mode, and the gain may be automatically raised in this set time.

Also, as shown in FIG. 1, the B image constructing section 17, the Doppler image constructing section 19 and the CFM constructing section 21 are disposed in parallel, and in the judging section 22, the B image judging unit 13 that judges on the basis of the B image, the Doppler signal judging unit 14 that judges on the basis of the Doppler signal, and the CFM judging unit 15 that judges on the basis of the CFM image are disposed in parallel. Here, means (not shown) is further disposed which switches between the mode that judges on the basis of the B image, the mode that judges on the basis of the Doppler signal and the mode that judges on the basis of the CFM image. Thus, the modes can be appropriately separately used as needed. The switching means may be the operation console 30, so that the operator can optionally switch modes.

Also, the control section 26 may automatically switch the switching means at predetermined time intervals so that the respective judging modes can be conducted at time intervals. In this manner, the judging modes are measured in order at time intervals, whereby the precision of detecting that the probe is left in the air can be improved.

The mode that judges on the basis of the B image, the mode that judges on the basis of the Doppler signal and the mode that judges on the basis of the CFM image may also be combined and simultaneously executed. For example, by combining the B image judging mode and the Doppler judging mode, the integrated value and variance information increase, and the precision of detecting that the probe is left in the air can be further improved.

Embodiment 3

A third embodiment of the ultrasonic diagnostic apparatus to which the present invention is applied will be described using FIG. 6, FIG. 7(B) and FIG. 12. The present embodiment is different from the first embodiment and the second embodiment in that instead of starting the freezing of the ultrasonic wave transmission system when it is detected that the probe 10 is left in the air, the energy of the drive signal of the probe 10 is reduced to be equal to or less than a set value. Thus, the same reference numerals will be given to elements having the same function and configuration as those in the first embodiment and the second embodiment, and description thereof will be omitted.

In the present embodiment, first, the condition of the drive signal when the temperature of the probe 10 left in the air does not rise is set. For example, whether or not the temperature of the probe 10 has risen is measured by changing the transmission voltage of the ultrasonic wave transmitted from the probe 10, the number of transmitted waves, the repetition frequency, and the scanning range of the ultrasonic beam. Then, the measured condition of the drive signal is set from the operation console 30 as a set value ($\alpha$).

Figure 6:
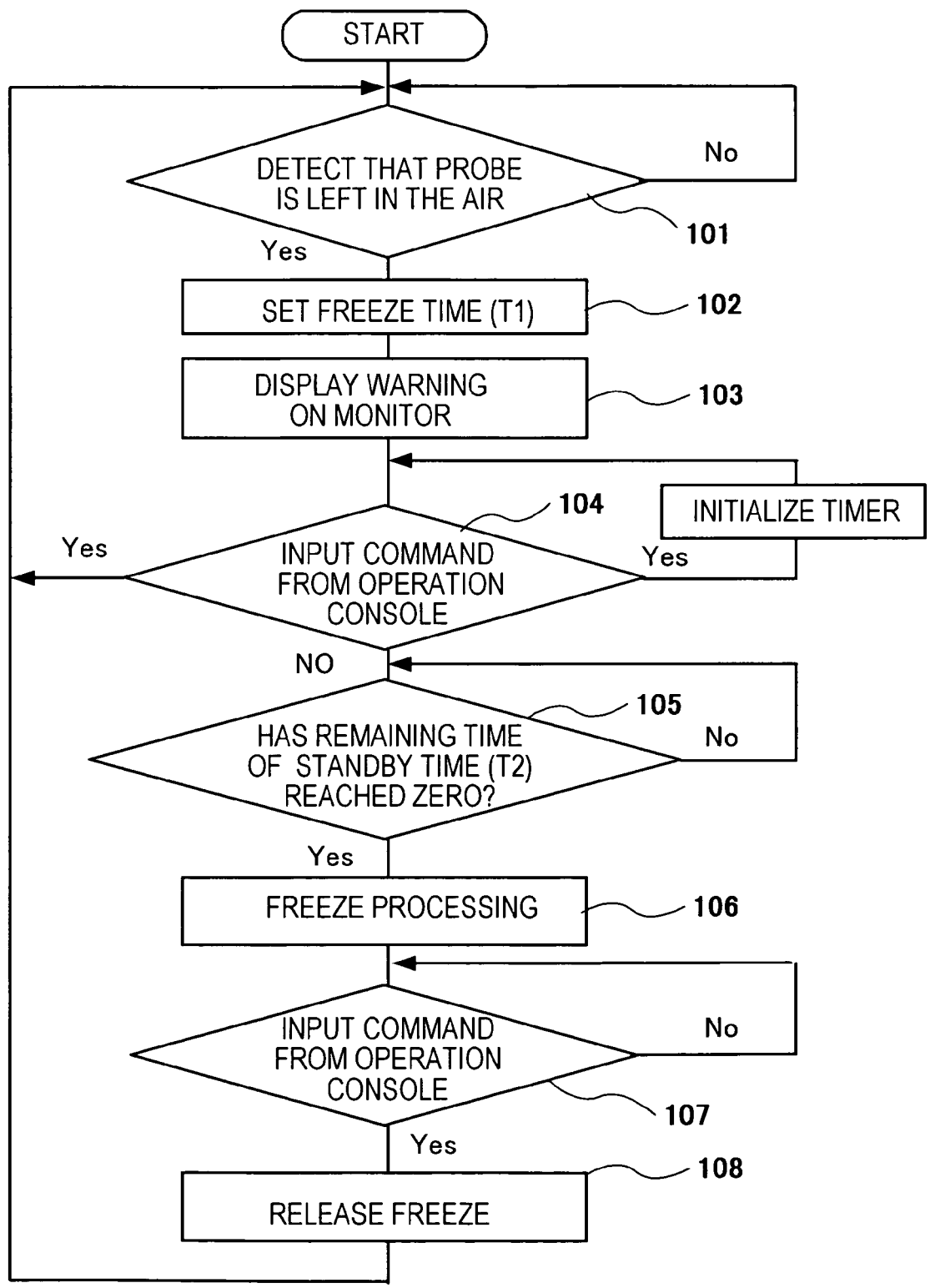
FIG. 6 is a flow chart showing a processing sequence.

Then, as shown in FIG. 6 and FIG. 7(B), when the standby time (T2) reaches zero in the processing of step 105, the drive signal supplied to the probe 10 from the transmitting/receiving section 12 is changed to become equal to or less than the set value ($\alpha$). Namely, the control section 26 issues a command to the transmitting/receiving section 12, whereby the transmission voltage, the number of transmitted waves, the repetition frequency, and the scanning range of the ultrasonic beam, which are transmission conditions of the ultrasonic wave from the probe 10, are reduced (Td). By reducing the energy of the drive signal supplied to the probe 10 from the transmitting/receiving section 12 to be equal to or less than the set value ($\alpha$) in this manner, the energy of the ultrasonic wave transmitted from the probe 10 is reduced. Thus, a rise in the temperature of the probe 10 can be suppressed even when the energy of the ultrasonic wave is converted into thermal energy inside the probe 10, so that it becomes possible to avoid deterioration of the probe resulting from the thermal heat cycle.

Also, because the ultrasonic wave is transmitted from the probe 10 even when the drive signal of the probe 10 is reduced to be equal to or less than the set value ($\alpha$), a diagnostic image can be obtained if it is at an observation site with a shallow depth. Thus, the efficiency of ultrasound diagnosis can be improved in comparison to when the ultrasonic wave transmission system is frozen.

Also, as shown in FIG. 12, a message representing the period of time until the drive signal of the probe 10 is reduced to be equal to or less than the set value ($\alpha$), i.e., the period of time until the image quality changes, may be displayed on the display section 25. Namely, when the drive signal of the probe 10 is reduced, sometimes the image quality of the B image obtained with the ultrasonic wave transmitted from the probe 10 deteriorates. Thus, it is preferable to display a message indicating this in order to inform the examiner that the image quality will deteriorate.

Embodiment 4

Figure 13:
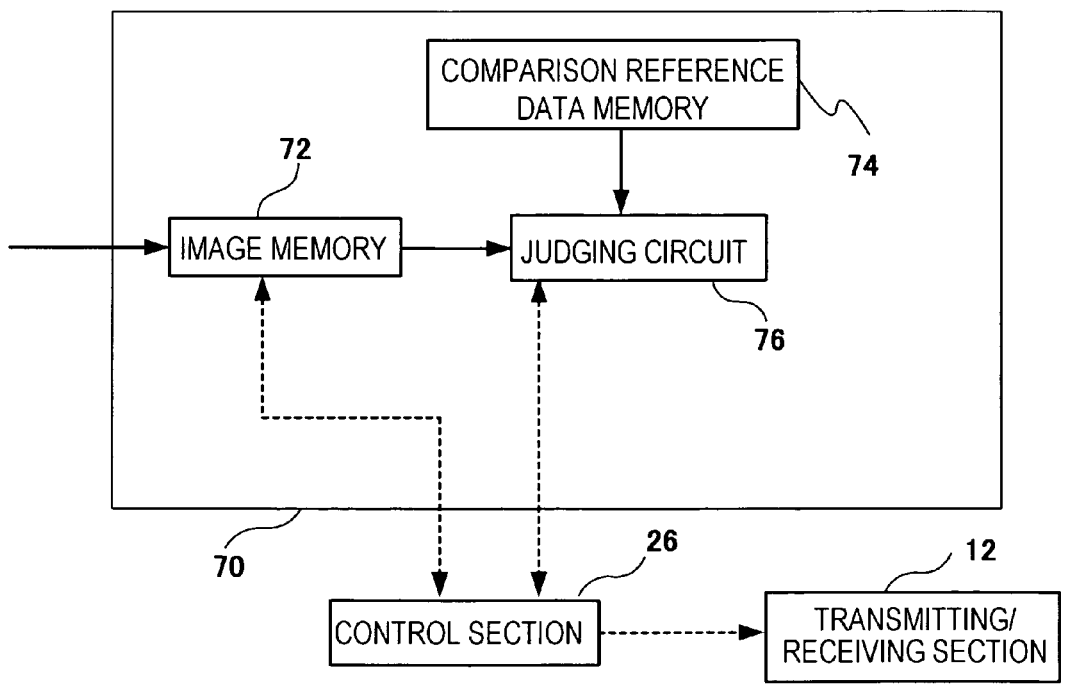
FIG. 13 is a diagram showing the configuration of a judging section.
Figure 14:
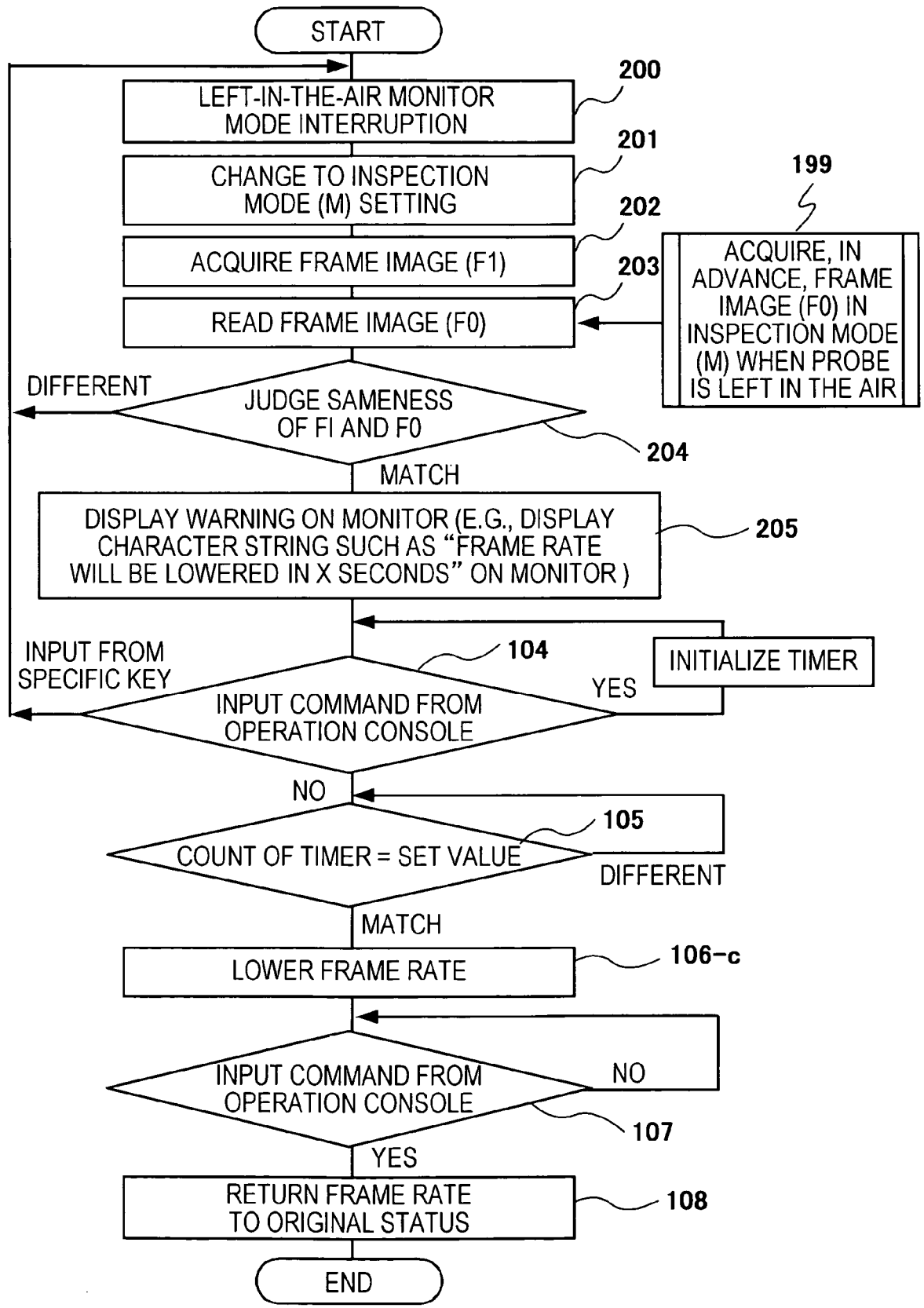
FIG. 14 is a flow chart showing a processing sequence.

A fourth embodiment of the ultrasonic diagnostic apparatus to which the present invention is applied will be described using FIG. 13 and FIG. 14. The present embodiment is different from the preceding embodiments in that the frame rate of the diagnostic image is reduced when the probe 10 is left in the air. Thus, the same reference numerals will be given to elements having the same function and configuration as those in the preceding embodiments, and description thereof will be omitted. FIG. 13 is a configural diagram of a judging section 70 in the present embodiment, and FIG. 14 is a flow chart describing the operation of the present embodiment.

In the present embodiment, the judging section 70 is disposed in place of the judging section 22 shown in FIG. 1. As shown in FIG. 13, the judging section 70 is configured by an image memory 72, a comparison reference data memory 74, and a judging circuit 76. The image memory 72 stores, as comparison data, the B image read from the frame memory. The comparison reference data memory 74 stores, as comparison reference data, the B image imaged when the probe 10 is left in the air. The judging circuit 76 compares the B image read from the image memory 72 with the B image read from the comparison reference data memory 74.

Figure 15:
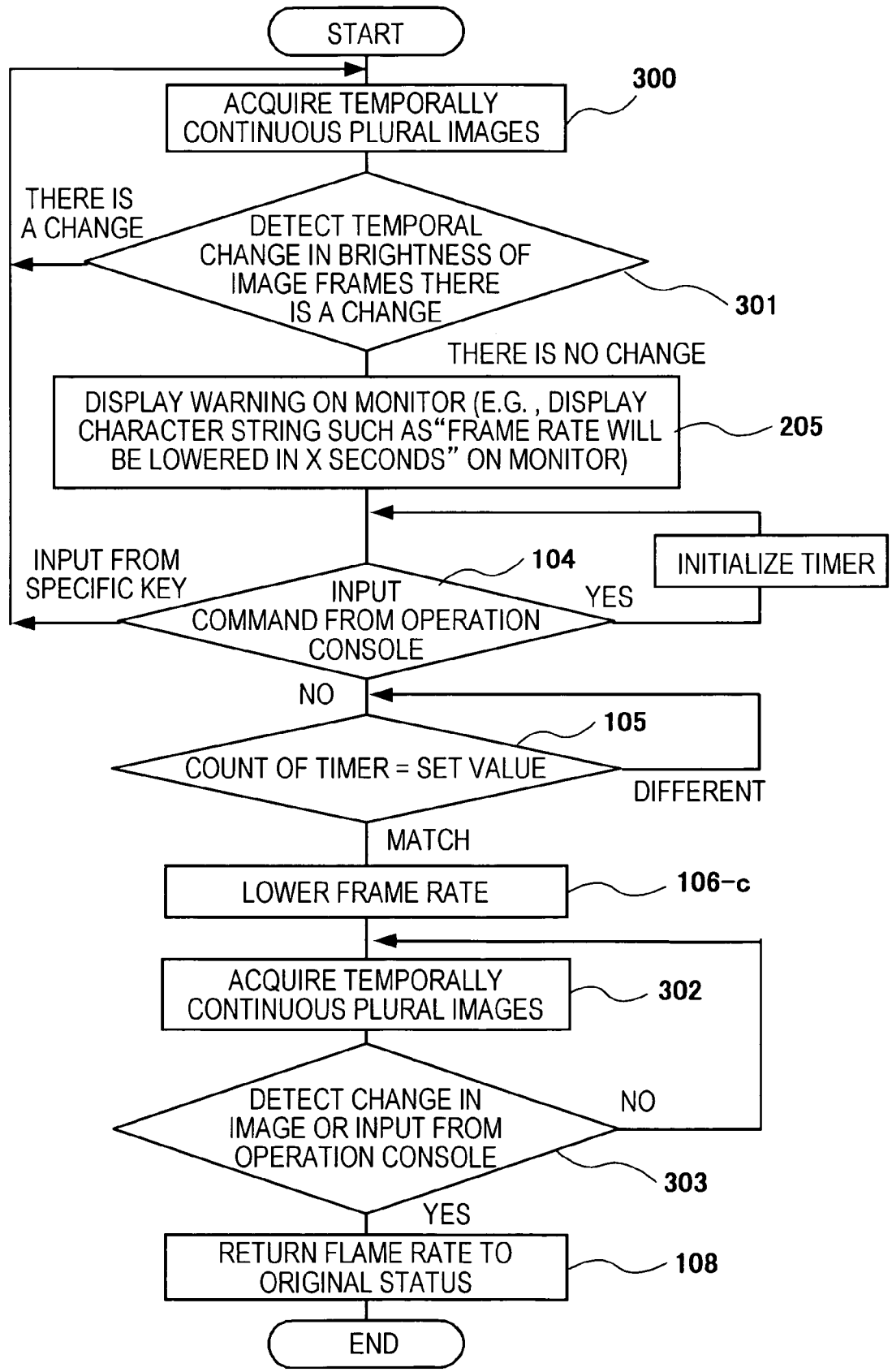
FIG. 15 is a flow chart showing a processing sequence.

The operation of the present embodiment will be described with reference to FIG. 14 and FIG. 15. The same reference numerals will be given to processing that is the same as the processing in FIG. 6. First, the comparison reference data are collected beforehand in order to judge that the probe 10 is left in the air (step 199). For example, when the probe 10 is left in the air, ultrasound imaging is executed and a frame image (F0) is acquired after the frequency, voltage, and number of waves of the ultrasonic waves transmitted from the probe 10 have been set to predetermined values (below, inspection mode M). The acquired frame image (F0) is stored in the comparison reference data memory 74 as comparison reference data. Comparison reference data are acquired for each type or product of the probe. Also, the comparison reference data may also be stored in a register of the control section 26.

Next, when the ultrasonic diagnostic apparatus is running, the mode judging whether or not the probe 10 is left in the air (below, left-in-the-air monitor mode) is interrupted per certain period of time (step 200). When switched to the left-in-the-air monitor mode, the ultrasonic wave transmitted from the probe 10 is changed to the frequency, voltage, and number of waves of the inspection mode M (step 201). Then, ultrasound imaging is executed and a frame image (F1) is acquired (step 202). The acquired frame image (F1) is stored in the image memory 72.

Next, the frame image (F0) is read from the comparison reference data memory 74 (step 203). The sameness of the read frame image (F0) and the frame image (F1) in the image memory 72 is judged by the judging circuit 76 (step 204). For example, the brightness value of each pixel of the frame image (F0) is integrated (Q0), and the brightness of each pixel of the frame image (F1) is integrated (Q1). The difference between the integrated value (Q0) and the integrated value (Q1) is computed, and it is judged whether or not the computed difference corresponds to a set range. When the difference does not correspond to the set range, the processing returns to step 200. When the difference corresponds to the set range, it is judged that the frame image (F0) and the frame image (F1) are substantially identical, and a notice message reducing the frame rate is displayed on the display section 25 (step 205). The notice message represents, for example, the period of time remaining until the reduction of the frame rate is started.

Then, after the same processing as in step 104 and step 105 of FIG. 6 is conducted, the reduction of the frame rate is started (step 106-c). For example, the repeat time of the ultrasonic waves transmitted from the probe 10 is lengthened, or the time from when reception of the reflection echo signal of one frame of a B image is completed to until transmission of the ultrasonic wave of the next frame is started is lengthened, whereby the frame rate of the diagnostic image drops. Because the ordinary frame rate of the B image is 30 Fps, it is set to 10 Fps, so as to fall within the range of ½ (15 Fps) to ⅙ (5 Fps) of 30 Fps, which is a frame rate sufficient for moving image reproduction. Thereafter, the same processing as in steps 107 and 108 of FIG. 6 is conducted. Thus, similar to the first to third embodiments, the fact that the probe is left in the air is accurately judged and a rise in the temperature of the probe can be suppressed.

Various aspects are conceivable in the processing of step 199. For example, when the probe 10 is left in the air, the comparison reference data may be acquired with all of the use conditions and not just the specific frequency, voltage, or number of waves. Also, the acquired comparison reference data may be stored in other storage means via a network. Also, in order to accommodate secular changes in the probe 10, the comparison reference data can be automatically updated or manually updated periodically. The comparison reference data may also be separately saved in the probe or the ultrasonic diagnostic apparatus by known technical means (e.g., Japanese Patent No. 1,997,704). The comparison reference data can also be collected while incrementally changing the gain of the reflection echo signal. The comparison reference data are appropriately selected and used from data acquired when the temperature of the probe 10 has started to rise, data when the temperature is rising, and data when the temperature has risen and become saturated. Also, when comparison reference data of different gains are necessary, they may be acquired while automatically changing the gain. The comparison reference data can also be acquired before product shipment.

Various aspects are also conceivable in the switching of the left-in-the-air monitor mode of step 200. For example, the mode may be switched to the left-in-the-air monitor mode when the operation console 30 has not been operated for a certain period of time. The mode can also be configured to be remotely switchable via a network automatically or manually. Also, a human sensor using infrared light, electrostatic capacitance or an ultrasonic wave may be installed in the ultrasonic diagnostic apparatus, and the mode may be switched as a result of the installed human sensor detecting the presence of the examiner. The ultrasonic diagnostic apparatus may also be configured to prohibit switching in order to conduct testing of the apparatus. Also, when the mode has been switched to the left-in-the-air monitor mode, a warning message representing that may be displayed, or a warning sound may be given.

Also, when the comparison reference data in all of the setting conditions (transmission voltage, frequency, number of waves, etc.) are gathered beforehand per probe, the fact that the probe is left in the air can be detected without switching the mode to the left-in-the-air monitor mode. For example, the imaging status of the ultrasonic diagnostic apparatus may be constantly monitored, and a setting that is the same as the setting during imaging may be extracted from a comparison reference data table. The extracted data may be stored in the comparison reference data memory 74 as the comparison reference data.

Also, the present embodiment was configured to acquire one frame image (F1) and judge, but the embodiment may also be configured so that temporally continuous frame images (F1, F2, etc., to Fm) are acquired and the temporal change in the brightness of the acquired frame images is detected. In this case, the temporal change in the brightness may be detected limited to a specific site, i.e., a set region of interest. In order to detect the temporal change in the brightness, known techniques can be applied, such as a method that compares the integrated values of the brightness of each frame image, a method that encodes the differences in the brightness, and a method that compares the absolute value of the differences in the brightness. Also, the present embodiment was described in relation to the B image, but it may also be made to accommodate the Doppler signal or CFM image.

Embodiment 5

A fifth embodiment of the ultrasonic diagnostic apparatus to which the present invention is applied will be described by FIG. 15. The present embodiment is different from the first to fourth embodiments in that energy consumption is reduced by judging not only that the probe is left in the air but also that a high frame rate is unnecessary during ultrasound diagnosis. Thus, the same reference numerals will be given to elements having the same function and configuration as those in the first to fourth embodiments, and description thereof will be omitted. FIG. 15 shows a flow chart describing the operation of the present embodiment. In the present embodiment, the B image judging unit 13 is used as the judging unit.

First, temporally continuous plural B images are acquired (step 300). For example, the B images f1 to fm are read in order from the frame memory, and the read B images f1 to fm are arranged in order and stored in the image memories 32-1 to 32-n. Step 300 is configured to interrupt per set time. Next, a temporal change in the brightness of the acquired B images is detected (step 301). Here, that which is different from the first embodiment is that it is not judged that the brightness of the B images corresponds to a set range, i.e., that they are whitish. Namely, the B image judging unit 13 correlates each inter-frame brightness, whereby it detects only the temporal change in the brightness.

When a temporal change in the brightness of the B images is detected, the processing returns to step 300. When none is detected, the same processing as in steps 205, 104 and 105 shown in FIG. 14 is conducted in order. Then, the frame rate is lowered by the processing of step 106-c. Namely, when it is judged that there is substantially no temporal change in the brightness of the B images, it is understood that a site accompanied by virtually no bodily movement (e.g., the abdomen) is presently being imaged, i.e., that the probe 10 is left in the air. In this case, it is judged that it is alright for the value of the frame rate not to increase that much, and the frame rate is lowered. In order to lower the frame rate, the repeat time of the ultrasonic wave transmitted from the probe 10 may be lengthened, or the period of time from when reception of the reflection echo signal of one frame of the diagnostic image is completed to until transmission of the ultrasonic waves of the next frame is started may be lengthened.

Next, temporally continuous plural B images are again acquired (step 302). The detection of a temporal change in the brightness of the acquired B images is conducted in the same manner as in step 301. (step 303). When it is judged that there is no temporal change in the brightness, the processing of step 302 is again executed. When it is judged that there is a temporal change in the brightness, processing that returns the frame rate to its original status is conducted (step 108). Namely, in step 303, by detecting that the brightness of the B images has changed temporally, it is understood that movement has arisen in the site presently being imaged, or that the probe 10 has been moved from being left in the air to contact the test subject. In this case, it is judged that a high frame rate is necessary, and the value of the frame rate is returned to its original value.

According to the present embodiment, it is accurately judged that a high frame rate is unnecessary during ultrasound diagnosis, and the frame rate is lowered. Thus, the drive energy inputted to the probe 10 is reduced and the consumed energy can be reduced. Moreover, even if the frame rate is lowered, there is virtually no change in the image quality of the image that is imaged when the diagnostic site is virtually unaccompanied by movement, so appropriate diagnosis can continue to be conducted. Similarly, even when the probe 10 is left in the air, there is similarly no temporal change in the brightness of the image, so processing which lowers the frame rate is executed and a rise in the temperature of the probe is suppressed.

Also, because the frame rate may be automatically lowered or raised as needed, the ease of use of the apparatus can be improved, such as it not being necessary for the examiner to manually switch the frame rate.

Embodiment 6

A sixth embodiment of the ultrasonic diagnostic apparatus to which the present invention is applied will be described using FIG. 16. The present embodiment is different from the first to fifth embodiments in that a frame correlation processing circuit 60 is used instead of the judging units in the judging section 22.

The frame correlation processing circuit 60 is configured to include an arithmetic processing circuit 62 and a frame memory 63. For example, the first B image outputted from the image constructing section 18 is stored in the frame memory 63 via the arithmetic processing circuit 62. The stored B image is fed back to the arithmetic processing circuit 62. The feedback B image and the B image next inputted to the arithmetic processing circuit 62 from the image constructing section 18 are simultaneously processed. For example, a temporal change in the brightness of the B images is detected by correlating the brightness per pixel. In this case, it is also detected that the brightness of the B images is whitish, so a threshold (P4) is delivered to the arithmetic processing circuit 62 from the control section 26. Thus, it is detected that the brightness has exceeded the preset threshold (P4) for a certain period of time or greater, so that it can be detected that the probe 10 is left in the air. Also, because this is realized by a single frame memory and not plural frame memories, the scale of the circuit configuration can be reduced.

An ultrasonic diagnostic apparatus pertaining to the present invention has been described on the basis of embodiments, but the present invention is not limited thereto. For example, it was detected that the probe 10 is left in the air on the basis of a temporal change in the brightness of the frame image, but this may also be detected on the basis of a temporal change in the reflection echo signal including a conveyance wave from the transmitting/receiving section 12. Namely, the reflection echo signal when the probe 10 is left in the air becomes different from the reflection echo signal from the tissue of a living organism because it is a multiple signal multiply reflected by an oscillator matching layer and lens inside the probe 10. Thus, by using the characteristic of the reflection echo signal as the judgment standard, it can be detected that the probe 10 is left in the air. The reflection echo signal differs for each type of probe, so it is good to measure, per probe, the reflection echo signal used as the comparison reference data. This may also be detected on the basis of a complex signal from the AD conversion unit.

Also, the acquired B image, the reflection echo signal, or the setting information of the detection mode may be recorded, and a graph with which temporal changes in the recorded information can be understood may be displayed, or a report or the like may be outputted. Thus, fluctuations in the B image accompanying secular deterioration of the probe can be understood, whereby accurate judgment in consideration of such fluctuations can be conducted.

Also, in order to fix the probe in a stand and appropriately conduct simulated imaging for measuring a phantom image, i.e., the performance of the apparatus, switching means may be disposed which can appropriately switch between a mode in which freezing is started and a mode in which freezing is not started when it is detected that the probe 10 is left in the air. Because phantom imaging is conducted while actually imaging the test subject, the acquired frame image or reflection echo signal resembles that which is acquired when the test subject is normally imaged.

Moreover, with respect to the notice message for warning that freezing will start, that the image quality will change, or that the frame rate will be lowered, the display size may be enlarged or the display color may be changed over time, or the notice message may be displayed while causing it to blink. Audio may be generated, and new symbols may be displayed. Thus, the clarity of the notice message improves, so that the examiner less fails to notice the message.

Also, the ultrasonic diagnostic apparatus of the present invention can comply with the index stipulated by the IEC because it can suppress a rise in the temperature of the probe 10 left in the air. Thus, ultrasound diagnosis can be safely conducted even when the probe 10 is again brought into contact with the body surface of the test subject.

According to the present invention, it can be accurately judged that the probe is left in the air and a rise in the temperature of the probe can be suppressed. Also, the constituent elements or functions described in the first to sixth embodiments can be appropriately combined, added, deleted, or switched.

The invention claimed is:

1. An ultrasonic diagnostic apparatus comprising:
    a probe that transmits/receives ultrasonic waves to/from a test subject;
    a transmitting section that supplies a drive signal to the probe;
    a receiving section that receives a reflection echo signal outputted from the probe;
    an image constructing section that reconstructs a diagnostic image on the basis of the received reflection echo signal;
    a display section that displays the diagnostic image constructed by the image constructing section;
    a control section that controls these sections; and
    a judging section configured to judge whether the probe has been left in the air based on comparison of a predetermined image obtained with the probe being left in the air to the diagnostic image information which is reconstructed from the image constructing section when the probe transmits/receives ultrasonic waves,
    wherein, when the judging unit judges that the probe is left in the air, the control section controls the drive signals supplied to the probe from the transmitting section so as to lengthen a time from when reception of the reflection echo signal of one frame of the diagnostic image is completed to a time when transmission of the ultrasonic wave of the next frame is started, thereby reducing the frame rate to a value that is lower than an ordinary frame rate.

2. The ultrasonic diagnostic apparatus of claim 1, wherein the judging section includes at least one of a B image judging unit that judges on the basis of a B image, a Doppler signal judging unit that judges on the basis of a Doppler signal, and a CFM judging unit that judges on the basis of a CFM image.

3. The ultrasonic diagnostic apparatus of claim 2, further comprising switching means that switches between the B image judging unit, the Doppler signal judging unit, and the CFM judging unit, wherein the switching means switches at desired time intervals.

4. The ultrasonic diagnostic apparatus of claim 1, wherein when the control section judges that the probe is left in the air, the control section stops the drive signal supplied to the probe from the transmitting section or reduces the energy of the drive signal to be equal to or less than a set value.

5. The ultrasonic diagnostic apparatus of claim 4, wherein the control section returns the energy of the drive signal supplied to the probe from the transmitting section, or the frame rate, to its original status on the basis of a command from an operation section, and transmits the ultrasonic waves to the test subject from the probe.

6. The ultrasonic diagnostic apparatus of claim 4, wherein the control section that generates a message representing the period of time until the energy of the drive signal supplied to the probe from the transmitting section is reduced to be equal to or less than the set value, and displays the generated message on the display section.

7. The ultrasonic diagnostic apparatus of claim 6, wherein the message is information giving notification of the period of time until the ultrasonic waves transmitted from the probe are stopped, the period of time until the image quality of the diagnostic image changes, or the period of time until the frame rate of the diagnostic image is reduced.

8. The ultrasonic diagnostic apparatus of claim 6, wherein the message is displayed while the display size, the display color, or other display aspects of the message change over time.

9. The ultrasonic diagnostic apparatus of claim 1, wherein the control section reduces a frame rate for an ordinary frame rate of the B image to be within a range of ½ to ⅙ of the ordinary frame rate.

10. The ultrasonic diagnostic apparatus of claim 9, wherein the reduced frame rate is ⅓ of the ordinary frame rate.

* * * * *